(12) United States Patent
Yonezawa

(10) Patent No.: US 9,161,686 B2
(45) Date of Patent: Oct. 20, 2015

(54) IMAGE PROCESSING APPARATUS AND IMAGE PROCESSING METHOD

(71) Applicant: CANON KABUSHIKI KAISHA, Tokyo (JP)

(72) Inventor: Keiko Yonezawa, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 117 days.

(21) Appl. No.: 14/140,657

(22) Filed: Dec. 26, 2013

(65) Prior Publication Data

US 2014/0185889 A1 Jul. 3, 2014

(30) Foreign Application Priority Data

Dec. 28, 2012 (JP) ................................ 2012-287252

(51) Int. Cl.
*A61B 3/00* (2006.01)

(52) U.S. Cl.
CPC ............. *A61B 3/0025* (2013.01); *A61B 3/0058* (2013.01)

(58) Field of Classification Search
CPC combination set(s) only.
See application file for complete search history.

(56) References Cited

U.S. PATENT DOCUMENTS

| | | | | |
|---|---|---|---|---|
| 5,868,134 | A * | 2/1999 | Sugiyama et al. | 600/300 |
| 6,198,532 | B1 * | 3/2001 | Cabib et al. | 356/456 |
| 6,276,798 | B1 * | 8/2001 | Gil et al. | 351/206 |
| 7,301,644 | B2 * | 11/2007 | Knighton et al. | 356/479 |
| 8,348,427 | B2 * | 1/2013 | Buckland et al. | 351/206 |
| 2007/0115481 | A1 * | 5/2007 | Toth et al. | 356/511 |
| 2010/0114079 | A1 * | 5/2010 | Myers et al. | 606/5 |
| 2010/0238401 | A1 * | 9/2010 | Kunath-Fandrei | 351/206 |
| 2011/0211161 | A1 * | 9/2011 | Gierhart et al. | 351/206 |
| 2011/0275931 | A1 * | 11/2011 | Debuc | 600/425 |
| 2012/0150029 | A1 * | 6/2012 | Debuc | 600/425 |
| 2013/0148081 | A1 * | 6/2013 | Tanaka et al. | 351/206 |

FOREIGN PATENT DOCUMENTS

| | | |
|---|---|---|
| CN | 1505491 A | 6/2004 |
| CN | 1650148 A | 8/2005 |
| CN | 1684627 A | 10/2005 |
| EP | 2457497 A1 | 5/2012 |
| JP | 2012-120890 A | 6/2012 |
| WO | 2012/025983 A1 | 3/2012 |

OTHER PUBLICATIONS

Arthur G. Bennett, Alicja R. Rudnicka, David F. Edgar, Improvements on Littmann's Method of Determining the Size of Retinal Features by Fundus Photography, Graefe's Archive for Clinical and Experimental Ophthalmology, 1994, 232(6):361-367, Springer-Verlag, Heidelberg DE, 1994.

(Continued)

*Primary Examiner* — Anand Bhatnagar
(74) *Attorney, Agent, or Firm* — Canon USA, Inc. I.P. Division

(57) ABSTRACT

An image processing apparatus includes an alignment unit configured to align a first fundus oculi image that is an aberration-corrected image of an eye being examined and a second fundus oculi image having a larger view angle and a lower resolution than the first fundus oculi image, by using a third fundus oculi image having a smaller view angle and a higher resolution than the second fundus oculi image; a distance acquisition unit configured to acquire a distance from a macula lutea of the eye being examined to a certain position in the first fundus oculi image aligned by the alignment unit; and an evaluation unit configured to evaluate the state of the eye being examined from the distance and information concerning photoreceptor cells included in the first fundus oculi image.

18 Claims, 14 Drawing Sheets

(56) References Cited

OTHER PUBLICATIONS

Kaccie Li, Pavan Tiruveedhula, Austin Roorda, Intersubject Variability of Foveal Cone Photoreceptor Density in Relation to Eye Length, Investigative Ophthalmology & Visual Science, Dec. 2010, 51(12):6868-6867, The Association for Research in Vision and Ophthalmology, Rockville, MD, 2010.

* cited by examiner

IMAGE PROCESSING APPARATUS AND IMAGE PROCESSING METHOD

BACKGROUND OF THE INVENTION

1. Field of the Invention

The embodiments disclosed herein relate to an image processing apparatus and an image processing method.

2. Description of the Related Art

For the purpose of early diagnosis of lifestyle diseases or diseases that rank high as a cause of blindness, the inspection of the fundus oculi of the human eye has been widely used. A scanning laser ophthalmoscope (SLO), which is an ophthalmological instrument that utilizes the principle of confocal laser scanning microscopy, is a device that uses laser light, which serves as measurement light, to raster-scan the fundus oculi to quickly obtain a high-resolution two-dimensional image from the intensity of the return light of the laser light. In recent years, adaptive optics SLOs (AO-SLOs) including an AO system configured to measure the aberrations of the eye being examined in real time by using a wavefront sensor and to correct the aberration of the measurement light that occurs in the eye being examined or the aberration of the return light of the measurement light by using a wavefront correction device have been developed. The AO-SLOs facilitate the acquisition of high-lateral-resolution two-dimensional images (hereinafter sometimes referred to as "AO-SLO images"). In addition, the photoreceptor cells in the retina are extracted from obtained two-dimensional retinal images, and the density or distribution of the photoreceptor cells is analyzed to attempt the diagnosis of a disease or the evaluation of drug response.

Image processing for detecting the photoreceptor cells may be performed with high accuracy by utilizing medical knowledge of photoreceptor cells. For example, it is known that the density of photoreceptor cells decreases as the distance from the macula lutea increases. In order to take advantage of this knowledge, users need to know the distance from the macula lutea to the region being analyzed.

Due to the smaller view angle of AO-SLO images than SLO images, an AO-SLO image, which is obtained by imaging the region in which the density is to be evaluated, does not generally include the macula lutea. Thus, it is difficult to know the exact distance from the macula lutea to the region. Accurate evaluation of the photoreceptor cells is therefore difficult to achieve.

SUMMARY OF THE INVENTION

There is provided an image processing apparatus including an alignment unit configured to align a first fundus oculi image that is an aberration-corrected image of an eye being examined and a second fundus oculi image that is an image having a larger view angle and a lower resolution than the first fundus oculi image, by using a third fundus oculi image that is an image having a smaller view angle and a higher resolution than the second fundus oculi image; a distance acquisition unit configured to acquire a distance from a macula lutea of the eye being examined to a certain position in the first fundus oculi image aligned by the alignment unit; and an evaluation unit configured to evaluate the state of the eye being examined from the distance and information concerning photoreceptor cells included in the first fundus oculi image.

Further features of the present invention will become apparent from the following description of exemplary embodiments with reference to the attached drawings.

DESCRIPTION OF THE EMBODIMENTS

Figure 1:
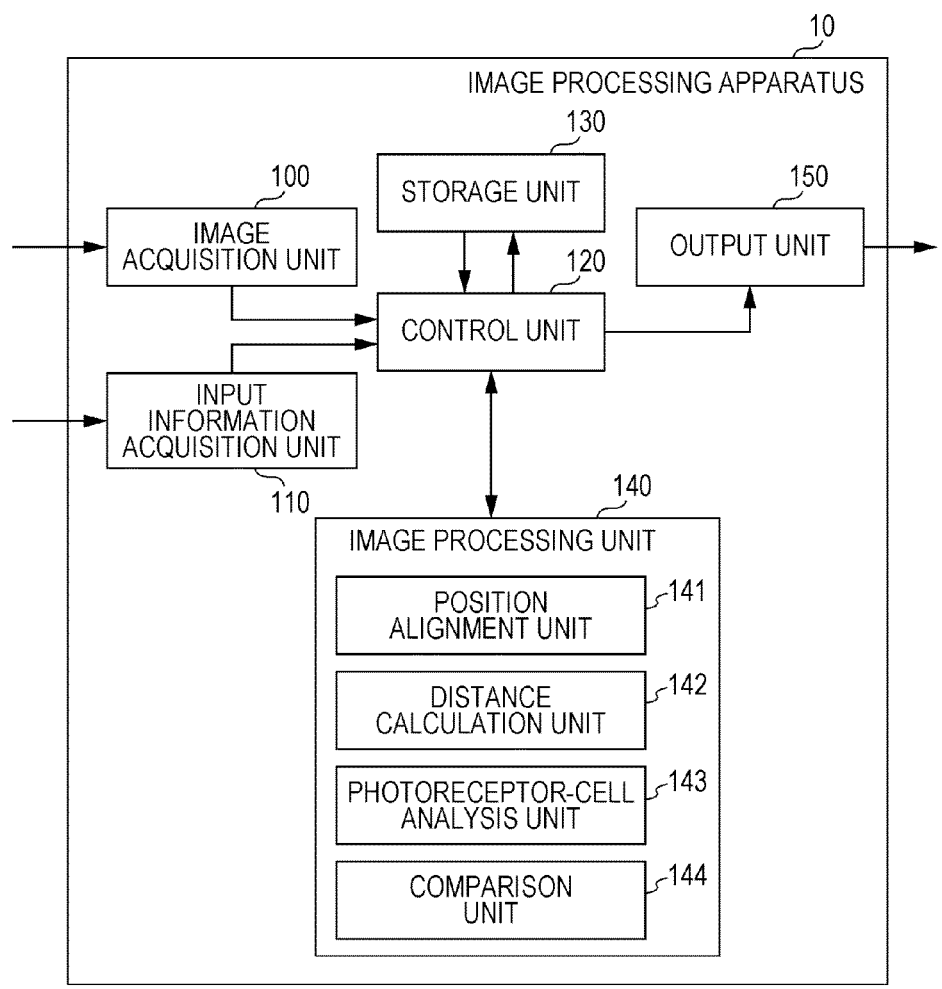
FIG. 1 is a diagram illustrating an example of a functional configuration of an image processing apparatus according to a first exemplary embodiment.

Some exemplary embodiments will be described in detail hereinafter with reference to the drawings.

Exemplary Embodiments

First Exemplary Embodiment

In a first exemplary embodiment, an AO-SLO apparatus acquires a captured retinal image by imaging the region in which the density of photoreceptor cells is to be evaluated and a range including the region of the macula lutea, and acquiring the distance from the macula lutea to the region in which the density is to be evaluated. The AO-SLO apparatus further detects the photoreceptor cells using an algorithm that reflects the distance from the macula lutea, and acquires the density of photoreceptor cells as a function of the distance from the macula lutea. The above processes will be described hereinafter.

Specifically, images are captured for the position of the macula lutea and for positions at distances of 0.5 mm and 1.0 mm from the macula lutea with changing fixation, at different resolutions. The distances from the macula lutea are illustrative, and are not limited to the values described above.

An aberration-corrected SLO image is a high-resolution image which is obtained by imaging a small range. Thus, a plurality of locations are imaged for each eye being examined. As a result of the imaging of a single location, a plurality of images specified by durations of imaging and frame rates are acquired. Hereinafter, a group of images obtained by the imaging of a single location will be sometimes referred to as "AO-SLO images". Since AO-SLO images can be captured with changing imaging ranges, AO-SLO images having different resolutions can be acquired. Furthermore, AO-SLO images for a plurality of locations having different resolutions, which are captured for each eye being examined, will be sometimes referred to as an "AO-SLO image group" for the eye being examined.

Through the alignment between AO-SLO images for the eye being examined, the positional relationship therebetween is established. Then, the macula lutea is detected from AO-SLO images in which the macula lutea appears, and the distance from the macula lutea to the region of each AO-SLO image is determined while the eye's axial length is taken into account. The photoreceptor cells are detected using AO-SLO images having sufficient resolutions, and an index such as the density of photoreceptor cells is acquired. Accordingly, the density of photoreceptor cells may be acquired as a function of the distance from the macula lutea.

One method taking the eye's axial length into account is described in, for example, the following publication: Bennett A G, Rudnicka A R, Edgar D F, Improvements on Littmann's method of determining the size of retinal features by fundus photography, Graefes Arch Clin Exp Ophthalmol, June 1994, 232 (6): 361-7. Specifically, the following calculation may be performed: $L=q\theta$, $q=0.01306 (x-1.82)$, where L denotes the distance from the macula lutea to a given position on the fundus oculi, $\theta$ denotes the oscillation angle of the scanner, and x denotes the eye's axial length. The method taking the eye's axial length into account is not limited to the method described above, and any other method may be used. For example, the method described in the following publication may be used: Li K Y, Tiruveedhula P, Roorda A, Intersubject Variability of Foveal Cone Photoreceptor Density in Relation to Eye Length Invest Ophthalmol Vis Sci., December 2010, 51 (12): 6858-67.

In this way, the use of a calculated distance from the macula lutea allows more accurate detection of photoreceptor cells. In addition, the density of photoreceptor cells, which is known to change with the distance from the macula lutea, may be acquired in association with the distance from the macula lutea.

Configuration of Image Processing Apparatus

FIG. 1 illustrates an example of a functional configuration of an image processing apparatus 10 according to this exemplary embodiment.

In FIG. 1, an image acquisition unit 100 acquires AO-SLO images that have been acquired by an AO-SLO apparatus. The acquired AO-SLO images are stored in a storage unit 130 through a control unit 120. The image acquisition unit 100 may acquire AO-SLO images by merely receiving AO-SLO images transmitted from the AO-SLO apparatus or by fetching, by itself, AO-SLO images saved in a memory or the like provided outside the image processing apparatus 10. That is, the term "acquire" or "acquisition", as used herein, at least includes mere reception and actively going to an AO-SLO apparatus to retrieve something.

An input information acquisition unit 110 acquires user input. An image processing unit 140 includes a position alignment unit 141, a distance calculation unit 142, a photoreceptor-cell analysis unit 143, and a comparison unit 144.

The image processing unit 140 performs alignment between the acquired AO-SLO images to determine the relative positions of the AO-SLO images, and acquires the distance from the macula lutea to a region being analyzed in accordance with the positional relationship between an AO-SLO image used to detect the macula lutea and an AO-SLO image to be analyzed. The image processing unit 140 performs photoreceptor-cell analysis while reflecting the acquired distances from the macula lutea, and calculates an index such as density.

Further, the image processing unit 140 compares the calculated index with normal-eye data saved in the storage unit 130, and generates a graph or an image that clearly represents the comparison results.

An output unit 150 outputs the calculated index or the comparison results to a display unit such as a monitor, and also outputs the processing results stored in the storage unit 130 to a database.

Processing Procedure of Image Processing Apparatus

Figure 2:
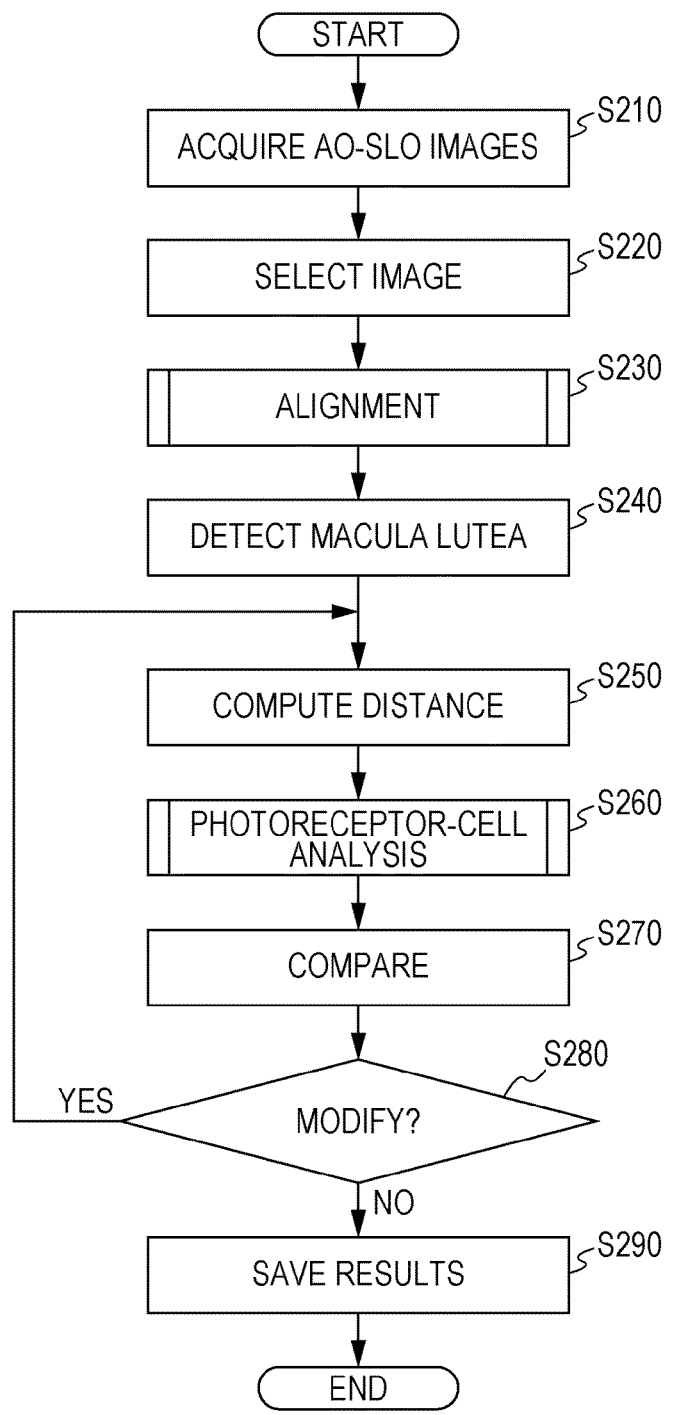
FIG. 2 is a flowchart illustrating an example of the processing procedure of the image processing apparatus according to the first exemplary embodiment.

Next, an example of the processing procedure of the image processing apparatus 10 according to this exemplary embodiment will be described with reference to a flowchart illustrated in FIG. 2.

Step S210

In step S210, the image acquisition unit 100 acquires a plurality of AO-SLO images of, for example, the retina of the eye being examined from an AO-SLO apparatus connected to the image processing apparatus 10.

Figure 3:
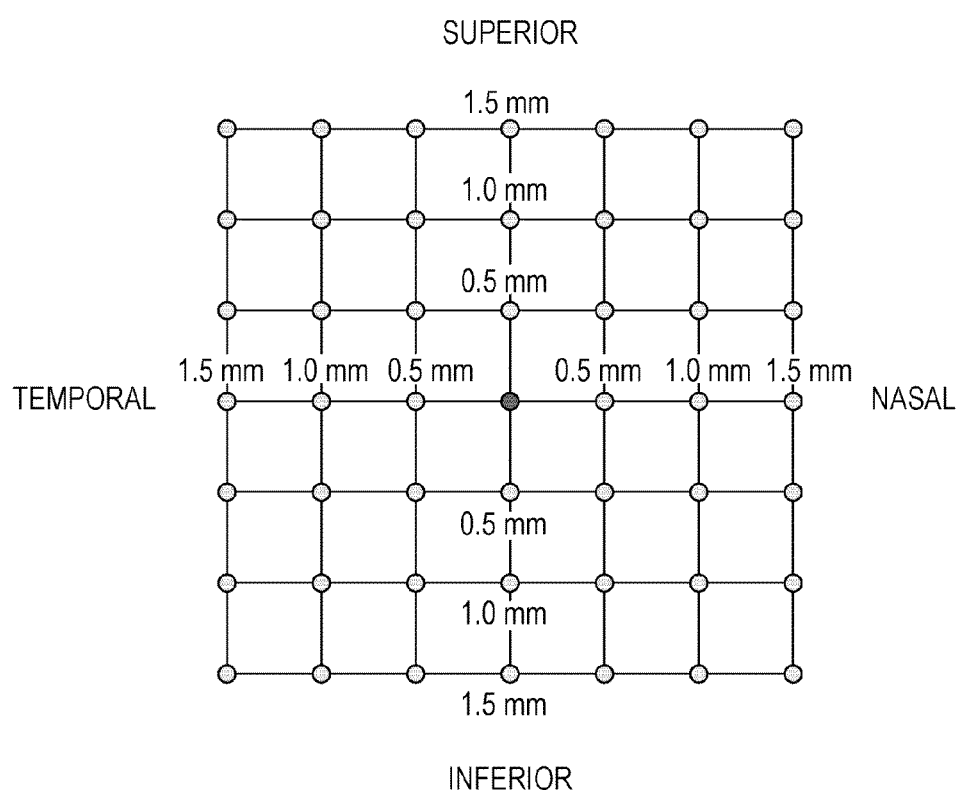
FIG. 3 is a diagram illustrating an example of a fixation lamp map used to operate the position at which a fixation lamp is placed.

An example of an imaging method for an eye being examined in order to perform photoreceptor-cell analysis will now be given. The AO-SLO apparatus used in this exemplary embodiment changes the position of a fixation lamp included in the AO-SLO apparatus so that the eye being examined may be imaged while gazing at different locations to obtain captured images of different locations in the retina. FIG. 3 illustrates an example of a fixation lamp map used to operate the position at which the fixation lamp is place. The fixation lamp map is displayed on, for example, the display unit. An examiner or user is able to change the position at which the fixation lamp is turned on to the desired position using a pointing device (or pointer) such as a mouse while referring to the displayed fixation lamp map.

In an example of the operation, first, the fixation lamp is placed while the center in the fixation lamp map illustrated in FIG. 3 is selected. The center position will be hereinafter sometimes referred to as a "reference position". The eye being examined may be imaged while gazing at the fixation lamp placed at the reference position to obtain a captured image of the region around the macula lutea.

In this state, a wide-field SLO (WF-SLO) image and a plurality of AO-SLO images having different resolutions are captured using the AO-SLO apparatus. The captured WF-SLO image is acquired by the image acquisition unit 100.

The WF-SLO image may have an image size of 8 mm×6 mm and a size of 533×400 pixels, by way of example. A wide range of the retina is imaged to acquire an entire image of the retina. The correspondence between the WF-SLO image and the AO-SLO images having small view angles allows the user to identify which location in the retina each of the AO-SLO image corresponds to.

The AO-SLO images are captured at three levels of resolution with imaged area sizes of 1.7 mm×1.7 mm, 0.82 mm×0.82 mm, and 0.34 mm×0.34 mm while a size of 400× 400 pixels is commonly used. These images are captured using the AO-SLO apparatus, and the captured images are acquired by the image acquisition unit 100. An AO-SLO image with an imaged area size of 1.7 mm×1.7 mm will be sometimes referred to as an "L image", an AO-SLO image with 0.82 mm×0.82 mm as an "M image", and an AO-SLO image with 0.34 mm×0.34 mm as an "S image". The imaged area sizes and the size of pixels described above are illustrative, and are not limited to the values described above. In other words, other values may be used. The M image or S image corresponds to an example of a first fundus oculi image. The WF-SLO image or L image corresponds to an example of a second fundus oculi image, and the L image or M image corresponds to an example of a third fundus oculi image.

While the duration of imaging and frame rate of an AO-SLO image may be changed, a frame rate of 32 frames per second and an imaging time of 2 seconds may be used here and an AO-SLO image may be formed of 64 images, by way of example.

Then, the fixation is shifted to the superior 0.5 mm position, and the examinee is instructed to gaze at the fixation lamp at the shifted position. In this state, M images and S images are captured. Likewise, the fixation is shifted to the nasal 0.5 mm position, to the inferior 0.5 mm position, and to the temporal 0.5 mm position in this order, and M images and S images are captured. The order in which the fixation is shifted is not limited to the example described above, and the fixation may be shifted in any other order. The same applies to the following description.

The fixation is further shifted to the superior 1.0 mm position, and the examinee is instructed to gaze at the fixation lamp at the shifted position. In this state, M images and S images are captured. Likewise, the fixation is shifted to the nasal 1.0 mm position, to the inferior 1.0 mm position, and to the temporal 1.0 mm position in this order, and M images and S images are captured.

Figure 4:
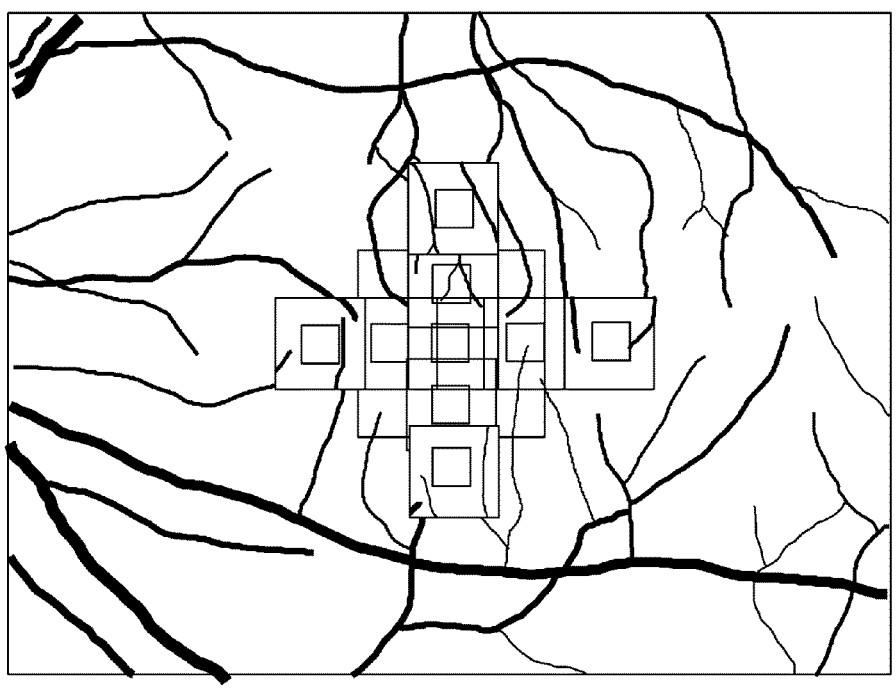
FIG. 4 is a diagram illustrating an example of a captured WF-SLO image and AO-SLO image group.

FIG. 4 schematically illustrates a WF-SLO image and an AO-SLO image group which are captured for each eye being examined in the way described above. In FIG. 4, the captured L, M, and S images are displayed so as to be superimposed on the WF-SLO image on the basis of only the information on the positions of the fixation.

As illustrated in FIG. 4, it may be found that the S images captured at the 0.5 mm and 1.0 mm positions do not overlap, whereas the M images captured at the 0.5 mm and 1.0 mm positions overlap. S images would be more appropriate for better resolving of the photoreceptor cells. However, the imaging of the photoreceptor cells up to the 1.0 mm region by using only S images so that the S images overlap one another involves imaging at intervals of at least 0.3 mm, by way of example, which may lead to increased load on the examinee. For this reason, the locations to be analyzed are set to the 0.5 mm and 1.0 mm positions, at which S images are captured. In addition, M images are captured at the 0.5 mm and 1.0 mm positions of fixation so that the M images at least partly overlap. The overlapping of the M images allows the user to accurately identify the mutual positions of the M images, thereby allowing the user to accurately identify the positions of the S images.

If characteristic objects such as thick blood vessels appear in an S image, the S image may be directly associated with the WF-SLO image without capturing M images and/or L images, or may be associated with the WF-SLO image using either M images or L images. However, it may be generally difficult to accurately associate the S image with the WF-SLO image because the WF-SLO image has a lower resolution than AO-SLO images. Capturing a combination of aberration-corrected SLO images having a lower resolution than S images, such as M images or L images, enables accurate alignment with a reduced load on the examinee.

The acquired AO-SLO image group of the eye being examined is saved in the storage unit 130 through the control unit 120.

Step S220

In step S220, the input information acquisition unit 110 selects a reference frame from among the frames constituting an AO-SLO image saved in the storage unit 130.

As described with reference to step S210, by way of example, an AO-SLO image is constituted by 64 frames which are obtained by imaging the same location for 2 seconds. Because of the small movements of the eye being examined during fixation, shifts may occur in the imaging positions of the 64 frames, and a distortion may also occur in each frame. The user selects a frame that has a small distortion and that is in good imaging condition from among the 64 frames to obtain a reference frame.

While the user selects a reference frame by way of example, a reference frame may be selected by using software. For example, average values or variances of brightness may be calculated, and a frame having a large average value or variance may be selected. Alternatively, a frame in which a ring structure indicating the presence of the photoreceptor cells is clearly observed in the frequency analysis may be selected.

The reference frames selected for the respective AO-SLO images in the manner described above are saved in the storage unit 130 through the control unit 120.

Note that if a single AO-SLO image is captured at each position of fixation in step S210, the processing of step S220 is not executed.

Step S230

In step S230, which is an example of an aligning step, the position alignment unit 141 performs mutual alignment between the plurality of AO-SLO images acquired by the AO SLO apparatus, which are saved in the storage unit 130. The alignment is performed using the reference frames selected for the respective AO-SLO images.

Figure 5:
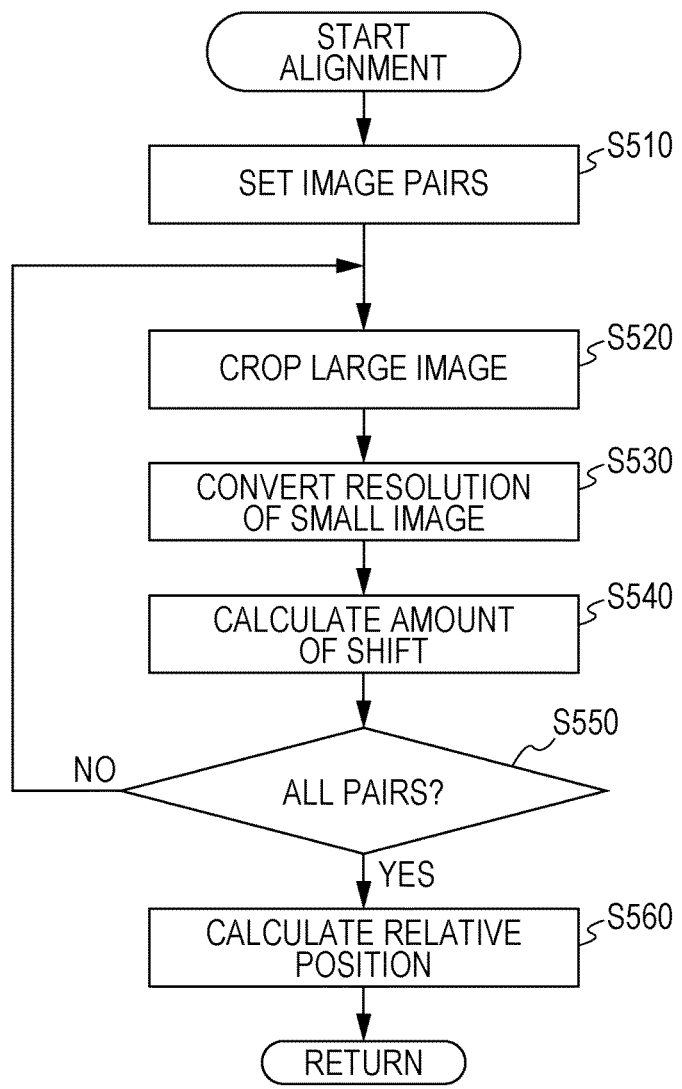
FIG. 5 is a flowchart illustrating an example of an alignment process illustrated in FIG. 2.

Since images having similar resolutions are aligned with high accuracy, for example, the WF-SLO image and the L images may be first aligned, and then the L images and the M images, followed by the M images and the S images, are aligned. There may be various alignment methods. Here, the phase-only correlation (POC) method is used by way of example. The details of alignment between the M image and the S image which are captured at the same position of fixation will be described with reference to a flowchart illustrated in FIG. 5.

Here, alignment is carried out between images having different resolutions. An image having a low resolution and a large view angle is referred to as a "large image", and an image having a high resolution and a small view angle is referred to as a "small image". Specifically, in the case of alignment between an M image and an S image, the M image is a large image and the S image is a small image. In the case of alignment between an L image and an M image, the L image is a large image and the M image is a small image.

Step S510

In step S510, the position alignment unit 141 sets a pair of two AO-SLO images between which alignment is to be performed from among the plurality of AO-SLO images acquired in step S210. There may be various setting methods. For example, first, the WF-SLO image and an L image at the reference position are selected as a pair. Then, the L image and an M image at the reference position are selected. Furthermore, the L image and M images at the four 0.5 mm positions (in the superior, nasal, inferior, and temporal directions) of fixation are selected.

After that, M images at the superior 0.5 mm and 1.0 mm positions are selected. Likewise, M images at the nasal, inferior, and temporal 0.5 mm and 1.0 mm positions are selected. Finally, an M image and an S image at the same position of fixation are selected.

The pairs of AO-SLO images set in the manner described above are saved in the storage unit 130 through the control unit 120. The procedure described above is an example, and images may be selected in any other order.

Step S520

In step S520, the position alignment unit 141 acquires the pairs of images selected in step S510 from the storage unit 130 through the control unit 120. The following description will be given in detail of an example in which acquired two images have different resolutions, for example, an example in which a large image is an M image and a small image is an S image at the same position of fixation.

An M image has an image size of approximately 820 µm, and an S image has an image size of approximately 340 µm, each of which has a size of 400×400 pixels. In these conditions, an M image overlaps an S image at a center thereof in the region of approximately 166 pixels. In the POC method, the fast Fourier transforms (FFTs) of the respective images are computed, and thus a region of 128×128 pixels in the center of the M image is cropped for high-speed operation. The size of the region to be cropped is not limited to the value described above, and may be a size to allow a large image and a small image to overlap. In a case where an L image and an M image are selected as a pair, for example, the center of the M image which is aligned based on the position of fixation is set as the center of the region to be cropped from the L image.

Step S530

In step S530, the position alignment unit 141 performs resolution conversion on the region in the small image among the image pair acquired in step S520 which corresponds to the region of the large image cropped in step S520. Specifically, an image of 128×128 pixels is generated using a region of 262.4 µm, which is given by 820×128/400, from the center of the S image. That is, the position alignment unit 141 corresponds to an example of a resolution conversion unit configured to convert the resolution of a high-resolution image into a resolution that is identical to the resolution of a low-resolution image in a case where an alignment unit performs alignment. The processing of step S520 and the processing of step S530 may be executed in opposite order, or may be executed simultaneously.

Step S540

In step S540, the position alignment unit 141 calculates an amount of shift for the portion (cropped large image) of the large image which has been cropped in step S520 and for the small image (low-resolution small image) whose resolution has been converted in step S530, using, for example, the POC method. Specifically, the cropped large image and the low-resolution small image are frequency-converted by FFTs. If the frequency-converted images are represented by F(u, v) and G(u, v), the position alignment unit 141 computes a phase-only correlation coefficient C(u, v) using the equation below.

$$C(u, v) = \frac{F(u, v)G(u, v)^*}{|F(u, v)G(u, v)^*|}$$

That is, the position alignment unit 141, which is an example of the alignment unit, performs alignment using the resolution-converted images.

The inverse FFT of C(u, v) is determined, and a peak value is detected. Accordingly, amounts of shift may be calculated.

The calculated amounts of shift are saved in the storage unit 130 through the control unit 120.

Step S550

In step S550, the position alignment unit 141 determines whether the amounts of shifts for all the image pairs set in step S510 have been calculated. If there is any image pair for which the amount of shift has not been calculated, the process returns to step S520, in which an amount of shift for the image pair is calculated. If the processing has been completed for all the image pairs, the process proceeds to step S560.

Step S560

In step S560, the position alignment unit 141 performs mutual alignment between images in each of the image pairs set in step S510 in accordance with the corresponding amount of shift calculated in step S540.

Specifically, the amount of shift (or the amount of displacement) between the WF-SLO image and the L image, which are captured at the reference position, the amount of shift between the L image and the M image, and the amount of shift between the M image and the S image are used to determine the amounts of shift of the L, M, and S images with respect to the WF-SLO image. Also, the amount of shift between the L image and the M image at the 0.5 mm position of fixation and the amount of shift between the M image and S image at the 0.5 mm position of fixation are used to determine the amounts of shift of the M and S images at the 0.5 mm position of fixation with respect to the WF-SLO image.

Figure 6:
FIG. 6 is a diagram illustrating an example of a superimposition image of the WF-SLO image and the AO-SLO image group which have been aligned in position.

The mutual positions of all the AO-SLO images are determined in a way similar to that described above, and a superimposition image in which images are superimposed on one another so that, for example, images having large imaged areas underlie images having small imaged areas at corresponding positions is generated. That is, the position alignment unit 141 aligns the images in accordance with the calculated amounts of shift. FIG. 6 illustrates an example of a superimposition image in which the AO-SLO image group illustrated in FIG. 4 is mutually aligned. The superimposition image illustrated in FIG. 6 is displayed on the display unit such as a monitor using the output unit 150. Specifically, the output unit 150 causes a first image and a second image which are aligned by an alignment unit to be displayed on a display unit in such a manner that the first image and the second image are superimposed on each other. In FIG. 4, since the AO-SLO image group is placed on the basis of only the positions of fixation, blood vessels and the like deviate in position. In FIG. 6, in contrast, images having different resolutions are used to perform alignment stepwise, resulting in the AO-SLO images being placed at the correct positions. That is, the position alignment unit 141 aligns the WF-SLO image and the S images through the M images and the L images. The position alignment unit 141 corresponds to an example of an alignment unit configured to align a first fundus oculi image that is an aberration-corrected image of the eye being examined and a second fundus oculi image having a larger view angle and a lower resolution than the first fundus oculi image by using a third fundus oculi image having a smaller view angle and a higher resolution than the second fundus oculi image. More specifically, the position alignment unit 141, which is an example of the alignment unit, aligns a plurality of first fundus oculi images and a plurality of second fundus oculi images, which are obtained by imaging different positions on the fundus oculi of the eye being examined, by using a plurality of third fundus oculi images that are obtained by imaging the different positions on the fundus oculi. In a different aspect, the position alignment unit 141, which is an example of the alignment unit, aligns a first fundus oculi image and a second fundus oculi image in accordance with the result of alignment between the second fundus oculi image and a third fundus oculi image and the result of alignment between the third fundus oculi image and the first fundus oculi image.

While an example of a method for generating a superimposition image by using software has been described, positions may be manually aligned. In a specific method, in the image illustrated in FIG. 4 in which AO-SLO images are placed on the basis of the positions of fixation, the positions of the AO-SLO images are shifted by clicking and dragging a mouse while referring to characteristic objects such as blood vessels. Alignment may be performed manually only, or alignment may be performed by using software in the manner described above and then aligned images may be modified manually. In this case, for example, a pair of images consisting of an M image and an S image which are captured at the same position of fixation may be aligned first, and then the pair of aligned images may be aligned with the WF-SLO image and an L image.

The acquired superimposition image of the AO-SLO image group is saved in the storage unit 130 through the control unit 120. After the superimposition image is displayed on a monitor or the like through the output unit 150, the process returns to step S230.

Step S240

In step S240, the input information acquisition unit 110 acquires the position of the macula lutea from the superimposition image generated in step S220. The input information acquisition unit 110 saves the detected position of the macula lutea in the storage unit 130 through the control unit 120. The input information acquisition unit 110 corresponds to an example of a detection unit configured to detect the macula lutea.

There may be a plurality of possible methods for detecting the macula lutea. In one possible detection method, a user visually detects the macula lutea in an S image captured to be located at the center of fixation. This detection method is based on the knowledge that the brightness tends to decrease toward the region of the macula lutea, and may thus be implemented by software. In a specific method, for example, the differences between the brightness values of the respective pixels and the highest brightness value in the image are determined, and the centroid of the differences is determined and used as the macula lutea.

In another possible method, the center of an S image located at the center of fixation is used as the macula lutea since imaging is performed while the examinee is gazing at the fixation. That is, the input information acquisition unit 110, which is an example of the detection unit, detects the macula lutea from a first fundus oculi image including the macula lutea among a plurality of first fundus oculi images aligned by the alignment unit.

Here, AO-SLO images and a WF-SLO image are used. If it is possible to acquire other modality images such as optical coherence tomography (OCT) images obtained by imaging the same eye being examined, AO-SLO images and a WF-SLO image may be compared with these images to allow the user to select a position considered to be the macula lutea.

Since an S image has a higher resolution than any other image, it is possible to accurately detect the macula lutea. The macula lutea may also be detected using M images, L images, or a WF-SLO image.

Step S250

In step S250, which is an example of a distance acquiring step, the distance calculation unit 142 calculates the distances from the macula lutea to the regions of the respective AO-SLO images from the amounts of shift of the respective AO-SLO images with respect to the WF-SLO image, which are calculated in step S230, and the position of the macula lutea, which is acquired in step S240. That is, the distance calculation unit 142 corresponds to an example of a distance acquisition unit configured to acquire the distance from macula lutea of the eye being examined to a certain position in the first fundus oculi image aligned by the alignment unit. More specifically, the distance calculation unit 142, which is an example of the distance acquisition unit, acquires the distance from the macula lutea detected by the detection unit to a certain position in a first fundus oculi image not including the macula lutea among a plurality of first fundus oculi images aligned by the alignment unit.

The distance from the macula lutea to the region of each AO-SLO image may be determined by, for example, determining the coordinates of the center of the AO-SLO image, where the upper side of the superimposition image with respect to the macula lutea as a point of origin is represented by the Y-axis direction and the right side by the X-axis direction. The acquired coordinates of each AO-SLO image are referred to as "macular coordinates". The above distance is represented by $D_i$–M, where the amount of shift of each AO-SLO image i, which is determined in step S230, is represented by a vector $D_i$ and the position of the macula lutea acquired in step S240 is represented by a vector M from the center of the WF-SLO image. If the coordinates of the center of the AO-SLO image i are represented by $(X_i, Y_i)$, the distance $R_i$ from the macula lutea to the center of the AO-SLO image i may be determined by $$R_i = \sqrt{X_i^2 + Y_i^2}.$$

The determined macular coordinates of the respective AO-SLO images and the distances from the macula lutea are saved in the storage unit 130 through the control unit 120.

Step S260

In step S260, the photoreceptor-cell analysis unit 143 performs photoreceptor-cell analysis on the S images in the AO-SLO images acquired in step S210.

Figure 7:
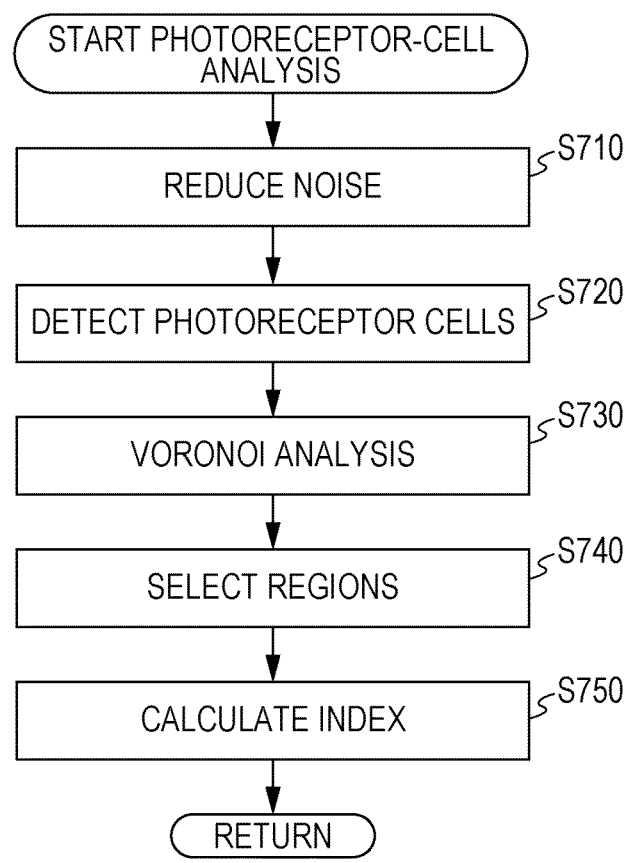
FIG. 7 is a flowchart illustrating an example of a photoreceptor-cell analysis process illustrated in FIG. 2.

FIG. 7 is a flowchart illustrating the details of the photoreceptor-cell analysis process.

Step S710

In step S710, the photoreceptor-cell analysis unit 143 performs preprocessing for photoreceptor-cell analysis on the basis of the reference frames of the AO-SLO images acquired in step S220. There may be a plurality of methods for the preprocessing. Here, noise reduction based on frequency analysis is given herein. Specifically, the reference frames are subjected to frequency conversion, and are subjected to inverse conversion after the application of a filter that eliminates the high-frequency component.

Since it is known that the photoreceptor cell size is approximately 2 μm around the region of the macula lutea, which is the smallest (the highest density of photoreceptor cells), the cut-off value (cut-off frequency) for removing the high-frequency component as noise is defined so that vibrations with a period shorter than 2 μm may be removed. Since it is also known that the density of photoreceptor cells decreases with increasing distance from the macula lutea, the cut-off frequency is changed in accordance with the distances acquired in step S250. For example, the photoreceptor cell size is defined to be 2 μm in the center of the region of the macula lutea, increasing by 1 μm every 0.5 mm of the distance from the macula lutea in the range from the center of the macula lutea to the 1.0 mm position, and to be 4 µm (fixed) at positions farther than the 1.0 mm position with respect to the macula lutea, and the cut-off frequency is determined in accordance with the distances from the macula lutea. That is, the photoreceptor-cell analysis unit 143, which is an example of the detection unit, changes a parameter to be used to detect the photoreceptor cells in accordance with the distances acquired by the distance acquisition unit.

Another method for noise reduction is to use a plurality of frames acquired as AO-SLO images to superimpose the AO-SLO images on one another. Specifically, after 64 frames of each AO-SLO image are subjected to registration processing by affine transformation or the like, averaging processing is performed on the region corresponding to the reference frame. The accuracy of this technique depends on the accuracy of the registration processing. The registration processing described above is followed by the removal of the high-frequency component based on frequency conversion described above.

The acquired images may be referred to as "preprocessed images".

Step S720

In step S720, the photoreceptor-cell analysis unit 143 detects the photoreceptor cells from the preprocessed images acquired in step S710. The photoreceptor-cell analysis unit 143 corresponds to an example of a detection unit configured to detect the photoreceptor cells from a first fundus oculi image.

Specifically, there is available a method for detecting local maximum values of the brightness of the preprocessed images. In this case, if the distance between points detected as local maximum values is smaller than the photoreceptor cell size, which is known as knowledge, it is determined that detection is influenced by noise and the detected points may be combined to increase robustness of detection. The photoreceptor cell size, used herein, may be calculated based on, similarly to step S710, the distance from the macula lutea to the region of the AO-SLO image to be analyzed, which is determined in step S250, to implement more accurate detection.

Among the detected points acquired in the manner described above, points having values greater than or equal to a specified threshold value are regarded as photoreceptor cells. The threshold value may be implemented as the lowest brightness value in an image (all the detected points are regarded as photoreceptor cells), the average brightness value in an image, or any other suitable value.

While an example of photoreceptor cell detection has been given here, the detection method is not limited to that described above and various methods are available. One possible method is to, for example, select pixels having brightness values greater than or equal to a threshold value to determine the centroid of a region where the selected pixels are connected. Another possible method is to calculate features of a sub-region and to detect photoreceptor cells using a pattern recognition technique. Specifically, Gabor features are calculated for a sub-region of, for example, 11×11 pixels. Gabor feature vectors that are obtained from a plurality of sub-regions centered on a detected point regarded as a photoreceptor cell and a plurality of sub-regions not including detected points regarded as photoreceptor cells are used to perform learning based on the support vector machine. Gabor features are calculated for a new target sub-region, and the results of the learning described above are used to determine whether the center of the sub-region is a photoreceptor cell or not.

In addition to the software-based detection described above, some of the detected points may be manually modified by a user. In this case, the input information acquisition unit 110 acquires the position of a detected point modified by the user among the detected points obtained in step S720.

Step S730

In step S730, the photoreceptor-cell analysis unit 143 performs Voronoi analysis on the detected points obtained in step S720.

Specifically, the following processing is performed on all the detected points obtained in step S720: An image is divided into regions by the perpendicular bisectors of close detected points to calculate Voronoi regions each including every detected point.

Step S740

In step S740, the photoreceptor-cell analysis unit 143 selects a region where an index is to be calculated from the results of the analysis in steps S720 and S730.

Figure 8A:
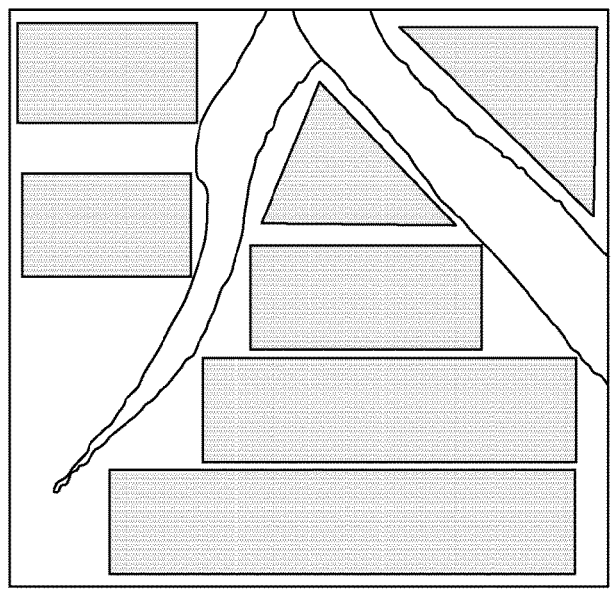
FIGS. 8A and 8B are diagrams illustrating an example of the selection of regions.
Figure 8B:
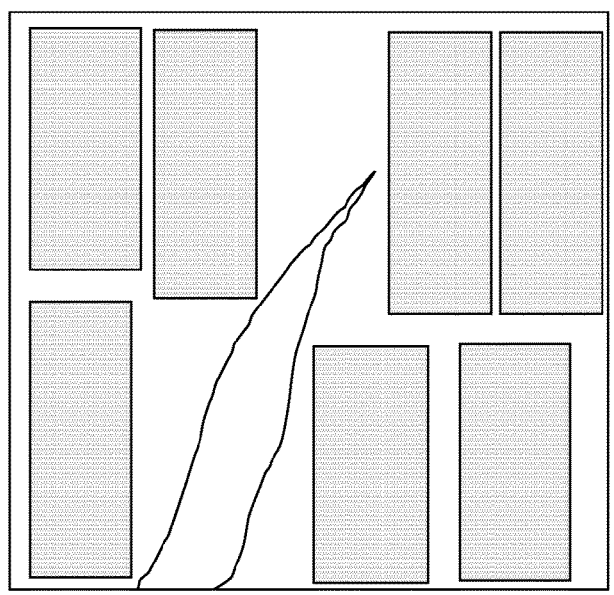

FIG. 8A illustrates an example of the selection of a region at the superior 0.5 mm position illustrated in FIG. 6, and FIG. 8B illustrates an example of the selection of a region at the temporal 0.5 mm position illustrated in FIG. 6. The regions may be rectangular, polygonal, oval, or of any other desired shape, and are set by the photoreceptor-cell analysis unit 143 in accordance with the user's click of the mouse or any other suitable operation. That is, the photoreceptor-cell analysis unit 143 corresponds to an example of a setting unit configured to set a region in a first fundus oculi image. The photoreceptor-cell analysis unit 143 may automatically set a region instead of in accordance with a user operation. After a region is automatically set, the region may be changed in accordance with a user operation.

If a blood vessel or the like is included in a region, the portion below the blood vessel has a low brightness, resulting in low accuracy in the detection of the photoreceptor cells. Accordingly, a region is selected so as to avoid including a blood vessel. That is, the photoreceptor-cell analysis unit 143, which is an example of the setting unit, sets a region so as not to include a blood vessel region which is included in a first fundus oculi image.

Furthermore, since the density of photoreceptor cells depends on their distance from the macula lutea, a landscape (or horizontally oriented) region is selected as a superior region, and a portrait (or vertically oriented) region is selected as a temporal region. Inferior and nasal regions are also selected in a similar way, that is, a landscape region is selected as an inferior region and a portrait region is selected as a nasal region. Accordingly, the variations of the distance from the macula lutea to a photoreceptor cell included in the same region may be reduced. That is, the photoreceptor-cell analysis unit 143 sets a region so that the width in the direction perpendicular to a straight line connecting an S image and the macula lutea is larger than the width in the direction parallel to the straight line. That is, the photoreceptor-cell analysis unit 143, which is an example of the setting unit, changes a method for setting the region in accordance with the positional relationship between a first fundus oculi image and the macula lutea. More specifically, the photoreceptor-cell analysis unit 143, which is an example of the setting unit, sets the region so that the width in the direction perpendicular to a straight line connecting a first fundus oculi image and the macula lutea is larger than the width in the direction parallel to the straight line.

The region may be set by, as described above, selecting an area having a certain size from a preprocessed image, or by setting a selected region for each detected point. For example, a circle with a size of 20 µm which is centered on each detected point may be set, and portions in the circles may be regarded as regions corresponding to the respective detected points. Regions may also be set in units of pixels at certain intervals without using detected points. Also in this case, for example, a circle with a size of 20 μm may be set for each of pixels selected at intervals of 10 pixels in the vertical and horizontal directions, and regions included in the circles may be used as selected regions.

Further, the distances from the macula lutea to the selected regions are calculated. The positions of the regions of the AO-SLO images from the macula lutea are calculated in step S250. The positions of the regions of the AO-SLO images calculated in step S250 and the positions of the selected regions in the AO-SLO images are used to calculate the distance from the macula lutea to the center of each of the selected regions. That is, the distance calculation unit 142, which is an example of the distance acquisition unit, acquires the distance from the position of the macula lutea to a certain position in a region (for example, the center of the region).

Step S750

In step S750, the photoreceptor-cell analysis unit 143 calculates an index for each of the regions selected in step S740 in accordance with the results acquired in steps S720 and S730.

Examples of the index include the number of detected points (the number of photoreceptor cells) determined in step S720, the density (the density of the photoreceptor cells) obtained by dividing the number of detected points by the area of the region, the average area per detected point in each of the selected regions, the distance to the nearest detected point determined in step S730, and the ratio of hexagonal Voronoi regions to the others. In addition to the index described above, the lateral width, longitudinal width, and area of the regions may be displayed. Additionally, the ideal distance to the nearest detected point, the ratio of the actual distance to the nearest detected point to the distance to the nearest detected point, and the like may also be displayed. The distance from the macula lutea may also be displayed.

The results of the photoreceptor-cell analysis and the acquired index or indices are saved in the storage unit 130 through the control unit 120. Then, the process returns to step S260.

Step S270

In step S270, which is an example of an evaluating step, the comparison unit 144 compares an index acquired as a result of the photoreceptor-cell analysis in step S260 with the normal-eye data saved in the storage unit 130, which is an example of reference information.

Figure 9A:
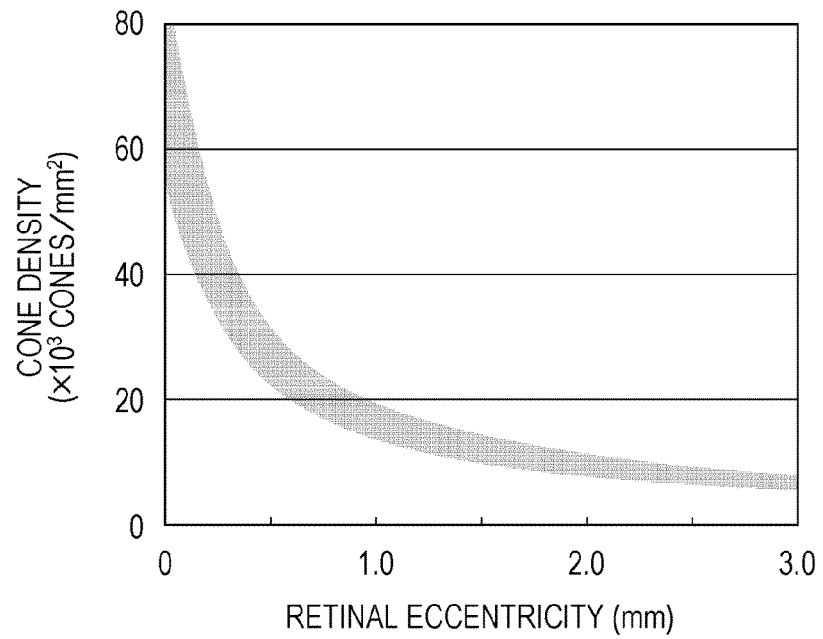
FIGS. 9A and 9B are diagrams illustrating an example of the relationship between a normal-eye distribution and detection results.
Figure 9B:
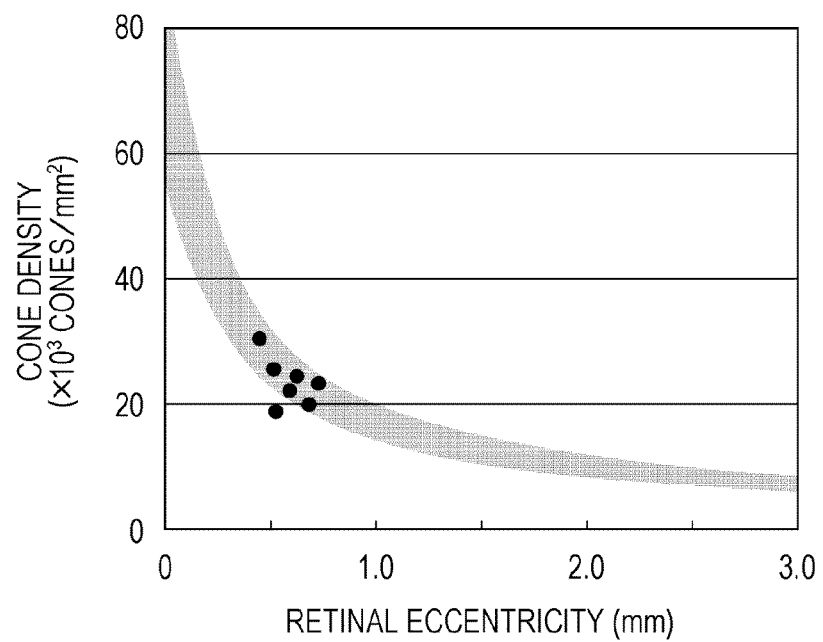

FIG. 9A illustrates an example of the relationship in the normal eye between the density of photoreceptor cells, which is an example of information concerning the photoreceptor cells, and the distance from the macula lutea. The shaded range in the illustrated graph represents the range of variations of the normal eye. FIG. 9B illustrates an example of the plot of the index of the density of photoreceptor cells for the selected regions illustrated in FIG. 8B, which is acquired in step S260. As illustrated in FIG. 9B, the normal-eye data corresponding to the distance from the macula lutea and the detected density of photoreceptor cells are compared. As may be seen, six regions out of the selected regions are included in the normal range and one region deviates from the normal range. That is, the comparison unit 144 corresponds to an example of an evaluation unit configured to evaluate the state of the eye being examined from the distance from the macula lutea to a certain position in a first fundus oculi image and information concerning photoreceptor cells included in the first fundus oculi image. More specifically, the comparison unit 144, which is an example of the evaluation unit, evaluates the state of the eye being examined from the distance to a certain position in a region and information concerning photoreceptor cells in the region. As described above, furthermore, the comparison unit 144, which is an example of the evaluation unit, compares the information concerning the photoreceptor cells with reference information based on the distance.

Figure 10A:
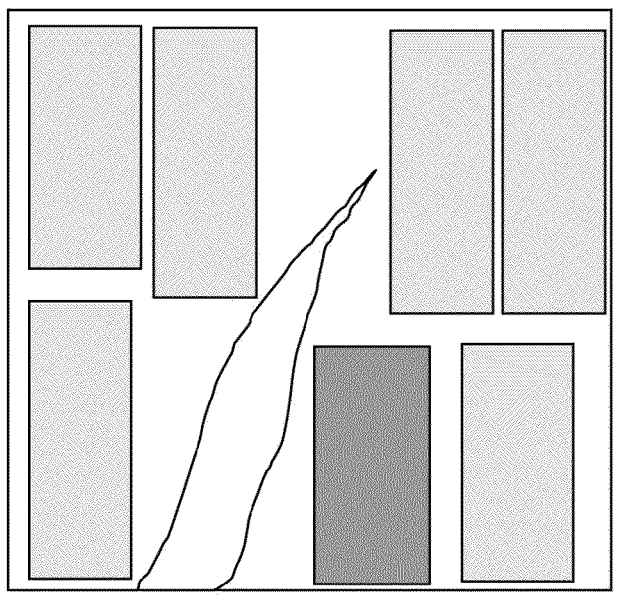
FIGS. 10A and 10B are diagrams illustrating an example of a deviation from the normal-eye distribution.

If a region deviates from the normal range, the output unit 150 causes a region deviating from the normal range among the regions illustrated in FIG. 8B to be displayed on the display unit such as a monitor in a manner illustrated in FIG. 10A in order to clearly identify which region deviates from the normal range. That is, the output unit 150 corresponds to an example of a display control unit configured to cause a first fundus oculi image to be displayed on a display unit in display form based on a result of the comparison. For example, the graph illustrated in FIG. 9B and the regions illustrated in FIG. 10A are displayed on the display unit side by side, allowing the user to easily identify a value deviating from the normal range and the corresponding one of the selected regions.

The graph illustrated in FIG. 9B and the regions illustrated in FIG. 8B may be linked with each other. The diagrams illustrated in FIGS. 8B and 9B may be displayed on the display unit side by side, and, for example, a point on the graph illustrated in FIG. 9B may be clicked on, thereby implementing edge enhancement of the corresponding one of the regions illustrated in FIG. 8B. Accordingly, the correspondence relationship may be more clearly identified.

Figure 10B:
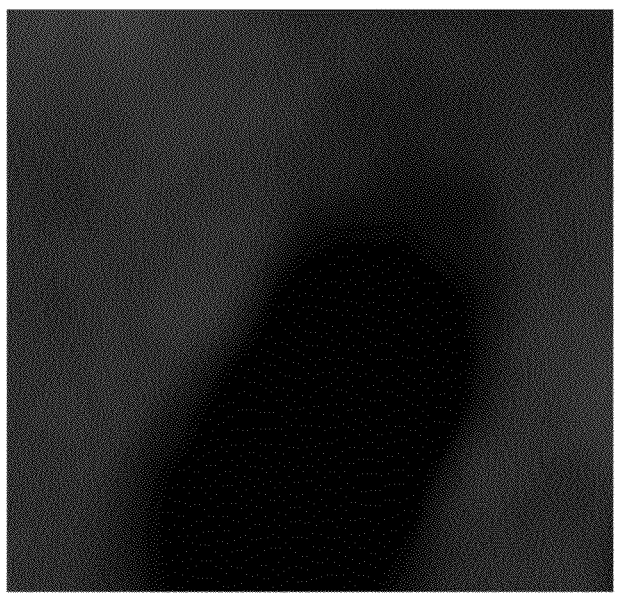

Furthermore, in the selection of regions in step S740, selected regions may be set in units of detected points or in units of pixels at certain intervals. For example, in a case where regions are selected at intervals of 10 pixels in the vertical and horizontal directions, each of the regions can be compared with the normal-eye distribution. FIG. 10B illustrates an example in which the above processing is performed on the regions illustrated in FIG. 8B. In FIG. 10B, the regions are displayed in color gradations in accordance with the deviation from the normal distribution average value in such a manner that regions deviating from the average value are displayed in dark color. Regions deviating more from the normal range may be displayed in lighter color or may be displayed in darker color. That is, the output unit 150, which is an example of the display control unit, changes the lightness of the first fundus oculi image in accordance with the difference between the information concerning the photoreceptor cells and the reference information corresponding to the distances.

The output unit 150 may further measure the area of a region out of the range of the normal distribution illustrated in FIG. 9A, and present the measurement result. That is, the output unit 150, which is an example of the display control unit, presents the area of a region in the first fundus oculi image for which the difference between the information concerning the photoreceptor cells and the reference information corresponding to the distances is greater than or equal to a certain value.

Figure 11:
FIG. 11 illustrates an example in which images indicating an example of deviations from the normal-eye distribution are displayed so as to be placed on the superimposition image.

FIG. 11 illustrates an example in which images generated for the respective AO-SLO images in the manner illustrated in FIG. 10B are displayed so as to be placed on the superimposition image illustrated in FIG. 6. The index indicating the degree of progress of the disease may be, for example, as a function of the distance from the macula lutea, the ratio of the area of an abnormal region to the entire area. Images generated in the manner illustrated in FIG. 10A may be displayed so as to be placed on the superimposition image illustrated in FIG. 6.

Step S280

In step S280, the input information acquisition unit 110 determines whether or not the user modifies the results of analysis and the results of comparison therebetween presented in step S270. In this case, the user may modify the alignment of each of the AO-SLO images in step S230 and the detection of the macula lutea in step S240.

Specifically, if it is determined that the alignment of an AO-SLO image in step S230 is incorrect, the user may change the position of the AO-SLO image. The user may also change the position of the macula lutea determined in step S240.

If no modification is to be performed by the user, the process proceeds to step S290. If modification has been performed, the process returns to step S250, in which the distances are calculated again based on the modified position of the macula lutea and the modified position of each AO-SLO image. Then, the subsequent processing is performed.

Step S290

In step S290, the control unit 120 saves the processing results stored in the storage unit 130, such as the calculated index and the comparison results, in a database.

With the configuration described above, a plurality of AO-SLO images acquired by an AO-SLO apparatus may be analyzed and an index may be calculated while the positional relationship with the macula lutea, which is not included in the same AO-SLO image, is taken into account.

Second Exemplary Embodiment

In the first exemplary embodiment, by way of example, a superimposition image created from a plurality of AO-SLO images having different resolutions is used to acquire the distance from the macula lutea to the region of the AO-SLO image to be analyzed, and analysis and evaluation that reflect the acquired distance are performed.

In a second exemplary embodiment, analysis and evaluation are performed using information on a lesion or the like detectable on a superimposition image.

In the hereditary diseases of the photoreceptor cells, as is known in the art, particular ring-shaped structures are observed in accordance with the progress of the diseases. Such ring structures are difficult to identify on high-resolution and low-view-angle images. Such ring structures may be identified on low-resolution but high-view-angle images. The following description will be given of a method for extracting the above-described structure from a high-view-angle image and changing the processing to be performed on a high-resolution image accordingly.

The functional configuration of an image processing apparatus 10 according to this exemplary embodiment is similar to that illustrated in FIG. 1, and a description thereof is thus omitted.

Figure 12:
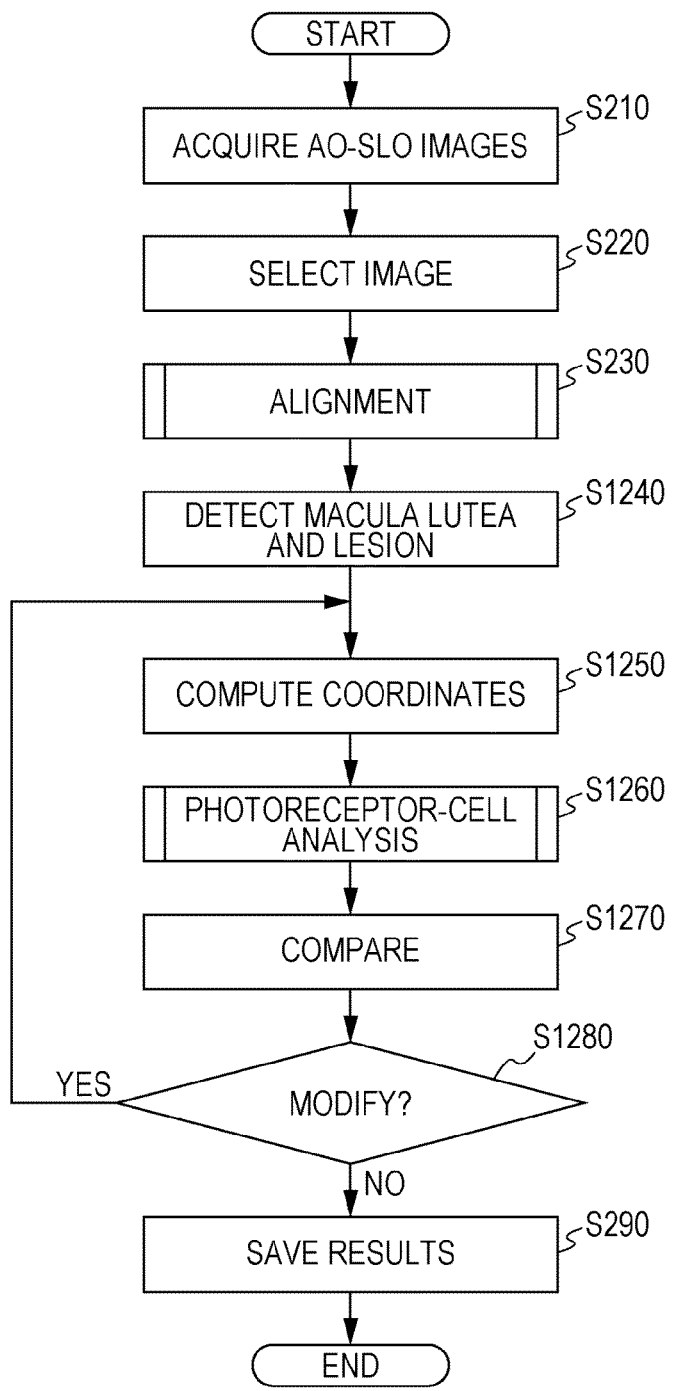
FIG. 12 is a flowchart illustrating an example of the processing procedure of an image processing apparatus according to a second exemplary embodiment.

The processing procedure of the image processing apparatus 10 according to this exemplary embodiment will be described with reference to a flowchart illustrated in FIG. 12. The processing of steps S210, S220, S230, and S290 is substantially the same as that described in the first exemplary embodiment, and a description thereof is thus omitted.

Step S1240

In step S1240, the input information acquisition unit 110 acquires the position of the macula lutea and the position of a lesion, which are detected by the user, in the superimposition image generated in step S220. Then, the detected positions of the macula lutea and the lesion are saved in the storage unit 130 through the control unit 120.

Figure 13:
FIG. 13 is a diagram illustrating an example of a lesion that appears on a superimposition image.

The method for detecting the macula lutea is substantially the same as that described above in the first exemplary embodiment. In a method for detecting a ring structure, a user visually detects a ring structure from a superimposition image. FIG. 13 illustrates an example of a superimposition image in which a ring structure appears. In FIG. 13, since the ring structure appears in a small region, a region created by four L images including the ring structure within the superimposition image is illustrated in an enlarged view. A user clicks the superimposition image with a mouse along the outline of the illustrated ring structure, thereby acquiring the outline.

There is still a method for acquiring a ring structure by extracting the ring structure from an image such as a fundus autofluorescence (FAF) image and placing the ring structure at a corresponding position in the superimposition image while referencing the positions of blood vessels and the like.

Step S1250

In step S1250, the distance calculation unit 142 calculates the coordinates of the region of each AO-SLO image with respect to the macula lutea as a point of origin, from the amount of shift of the AO-SLO image from the WF-SLO image, which is calculated in step S230, and from the position of the macula lutea acquired in step S1240. The distance calculation unit 142 further calculates the coordinates of the position of the lesion, which is acquired in step S1240, with respect to the macula lutea as a point of origin.

The method for determining the coordinates of the region of each AO-SLO image is substantially the same as the method described in the first exemplary embodiment. The coordinates of the position of the lesion may be acquired by converting the coordinate values acquired in step S1240 by mouse click or the like into a length on the superimposition image and by using the position of the macula lutea as a point of origin.

The determined AO-SLO images, and the position of the lesion from the macula lutea are saved in the storage unit 130 through the control unit 120.

Step S1260

In step S1260, the photoreceptor-cell analysis unit 143 performs photoreceptor-cell analysis on S images in the aberration-corrected SLO images acquired in step S210.

The step of photoreceptor cell analysis is performed in accordance with the method described above in the first exemplary embodiment. The following description will focus on the process for changing the processing in accordance with lesion information acquired in step S1240.

In general, the progress of the disease differs inside and outside the ring structure, and thus the photoreceptor cells are rendered in a different way. Although whether a nearly normal region is located inside or outside the ring depends on the disease, the photoreceptor cells generally degenerate in the region where the disease progresses and a structure other than the photoreceptor cells may be rendered in this region or a wide low-brightness region may be rendered in this region. For this reason, if the local maximum detection algorithm given in the first exemplary embodiment applies, a large amount of noise may be picked up, resulting in a reduction in the robustness of the algorithm.

In order to avoid the above situation, if the region to be subjected to photoreceptor-cell analysis is located on the side of the ring structure where the disease progresses, additional average filter processing is performed in the preprocessing of step S710. While an average filter is used here, the type of filter to be used is not limited to an average filter and any type of filter that leads to a reduction in noise, such as a Gaussian filter, may be used.

In addition, the threshold parameter used for the detection of step S720 is changed inside or outside the ring. Specifically, for example, the lowest brightness value of the image is used inside the ring, as in the first exemplary embodiment, whereas the average brightness value of the image is used outside the ring. The threshold parameter is changed in order to, as described above, increase robustness of detection in a case where the photoreceptor cells are not clearly rendered inside or outside the ring.

Furthermore, the detection of step S720 is based on pattern recognition, by way of example. In this case, desirably, results of learning are used for inside and outside the ring for each disease.

Step S1270

In step S1270, the comparison unit 144 compares the index acquired as a result of the photoreceptor-cell analysis in step S1260 with the normal-eye data saved in the storage unit 130.

Figure 14:
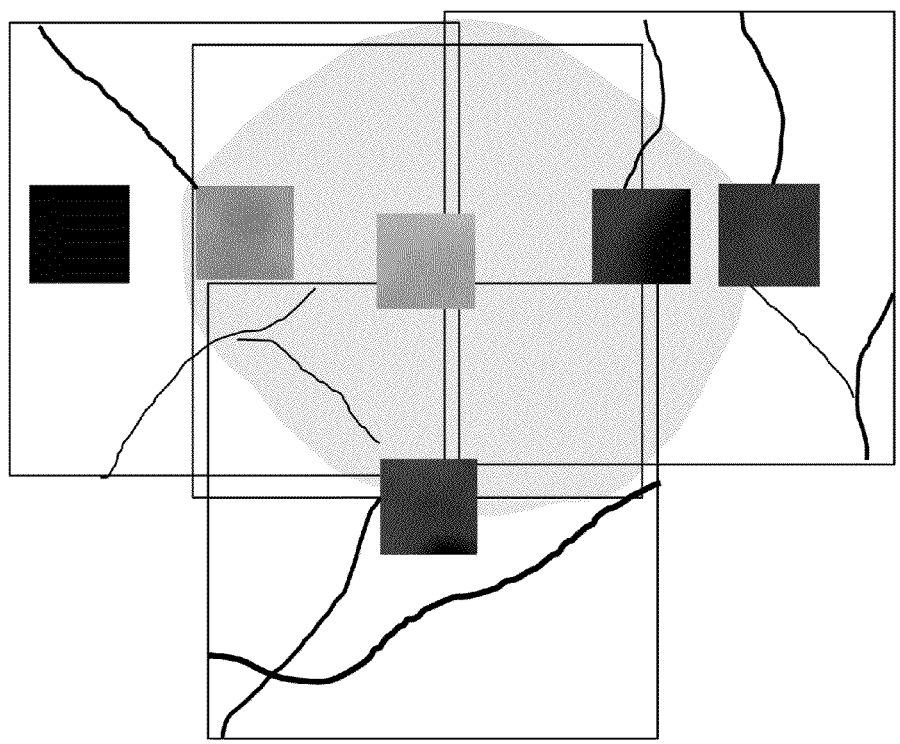
FIG. 14 is a diagram illustrating an example in which images indicating deviations from the normal-eye distribution are displayed so as to be placed on the superimposition image.

FIG. 14 illustrates results of processing similar to that illustrated in FIG. 11 which is performed on the respective S images illustrated in FIG. 13 through processing similar to that of step S270 in the first exemplary embodiment. In FIG. 14, there is an inconsistency between the lesion appearing in the superimposition image and an image created by comparing the results of the photoreceptor-cell analysis with the normal-eye distribution. Specifically, the S images located on the right side in FIG. 14 largely deviate from the normal distribution although they are inside the ring structure, and the S images located on the left side form a more normal distribution even though they are near the ring structure. In this case, the positions of the respective S images in the superimposition image might not have been correctly located, or the ring structure might not have been correctly acquired. Alternatively, what actually appears as a ring structure in the superimposition image might not correctly reflect the actual lesion. The former inconvenience, caused by alignment or the acquisition of a ring structure, may be overcome in step S1280. In the latter case, however, analysis through comparison with other modality images is needed, and the image illustrated in FIG. 14 is displayed to help the user elucidate the state of the disease.

Step S1280

In step S1280, the input information acquisition unit 110 determines whether or not the user modifies the results of analysis and the results of comparison therebetween presented in step S1270. In this case, the user may modify the alignment of each of the AO-SLO images in step S230 and the detection of the macula lutea and lesion in step S1240.

If it is determined that the user performs modification, the user resets the positions of the AO-SLO images and the positions of the macula lutea and the lesion. Then, the process returns to step S1250, in which the distances are recalculated based on the modified positions of the macula lutea and the lesion and the modified positions of the AO-SLO images. Then, the subsequent processing is performed. If no modification is performed by the user, the process proceeds to step S290.

Other Embodiments

Embodiments of the present invention can also be realized by a computer of a system or apparatus that reads out and executes computer executable instructions recorded on a storage medium (e.g., non-transitory computer-readable storage medium) to perform the functions of one or more of the above-described embodiment(s) of the present invention, and by a method performed by the computer of the system or apparatus by, for example, reading out and executing the computer executable instructions from the storage medium to perform the functions of one or more of the above-described embodiment(s). The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-287252 filed Dec. 28, 2012, which is hereby incorporated by reference herein in its entirety.

What is claimed is:

1. An image processing apparatus comprising:
an alignment unit configured to align a first fundus oculi image and a second fundus oculi image by using a third fundus oculi image, the first fundus oculi image being an aberration-corrected image of an eye being examined, the second fundus oculi image being an image having a larger view angle and a lower resolution than the first fundus oculi image, the third fundus oculi image being an image having a smaller view angle and a higher resolution than the second fundus oculi image;
a distance acquisition unit configured to acquire a distance from a macula lutea of the eye being examined to a certain position in the first fundus oculi image aligned by the alignment unit; and
an evaluation unit configured to evaluate the state of the eye being examined from the distance and information concerning photoreceptor cells included in the first fundus oculi image.

2. The image processing apparatus according to claim 1, wherein the alignment unit aligns the first fundus oculi image and the second fundus oculi image in accordance with a result of alignment between the second fundus oculi image and the third fundus oculi image and a result of alignment between the third fundus oculi image and the first fundus oculi image.

3. The image processing apparatus according to claim 1, further comprising:
a setting unit configured to set a region in the first fundus oculi image, wherein
the distance acquisition unit acquires a distance from the position of the macula lutea to a certain position in the region, and
the evaluation unit evaluates the state of the eye being examined from the distance to the certain position in the region and information concerning photoreceptor cells in the region.

4. The image processing apparatus according to claim 3, wherein the setting unit changes a method for setting the region in accordance with a positional relationship between the first fundus oculi image and the macula lutea.

5. The image processing apparatus according to claim 4, wherein the setting unit sets the region so that a width in a direction perpendicular to a straight line connecting the first fundus oculi image and the macula lutea is larger than a width in a direction parallel to the straight line.

6. The image processing apparatus according to claim 3, wherein the setting unit sets the region so that the region does not include a blood vessel region included in the first fundus oculi image.

7. The image processing apparatus according to claim 3, wherein the certain position is a center of the region.

8. The image processing apparatus according to claim 1, wherein the information concerning the photoreceptor cells is the density of the photoreceptor cells.

9. The image processing apparatus according to claim 1, further comprising:
a detection unit configured to detect the photoreceptor cells from the first fundus oculi image, wherein
the detection unit changes a parameter to be used to detect the photoreceptor cells in accordance with the distance acquired by the distance acquisition unit.

10. The image processing apparatus according to claim 1, wherein the evaluation unit compares the information concerning the photoreceptor cells with reference information corresponding to the distance.

11. The image processing apparatus according to claim 10, further comprising:
a display control unit configured to cause the first fundus oculi image to be displayed on a display unit in display form based on a result of the comparison.

12. The image processing apparatus according to claim 11, wherein the display control unit changes the lightness of the first fundus oculi image in accordance with a difference between the information concerning the photoreceptor cells and the reference information corresponding to the distance.

13. The image processing apparatus according to claim 12, wherein the display control unit presents the area of a region in the first fundus oculi image for which the difference between the information concerning the photoreceptor cells and the reference information corresponding to the distance is greater than or equal to a certain value.

14. The image processing apparatus according to claim 11, wherein the display control unit causes the first fundus oculi image and the second fundus oculi image aligned by the alignment unit to be displayed on the display unit in a such manner that the first fundus oculi image and the second fundus oculi image are superimposed on each other.

15. The image processing apparatus according to claim 1, further comprising:
a resolution conversion unit configured to convert the resolution of a high-resolution image into a resolution that is identical to the resolution of a low-resolution image in a case where the alignment unit performs alignment, wherein
the alignment unit performs alignment using an image whose resolution has been converted.

16. The image processing apparatus according to claim 1, further comprising:
a detection unit configured to detect the macula lutea, wherein
the alignment unit aligns a plurality of first fundus oculi images and a plurality of second fundus oculi images by using a plurality of third fundus oculi images, the plurality of first fundus oculi images and the plurality of plurality of second fundus oculi images being obtained by imaging different positions on the fundus oculi of the eye being examined, the plurality of third fundus oculi images being images captured at the different positions on the fundus oculi,
the detection unit detects the macula lutea from a first fundus oculi image including the macula lutea among the plurality of first fundus oculi images aligned by the alignment unit, and
the distance acquisition unit acquires a distance from the macula lutea detected by the detection unit to a certain position in a first fundus oculi image not including the macula lutea among the plurality of first fundus oculi images aligned by the alignment unit.

17. An image processing method comprising:
an aligning step of, using an alignment unit, aligning a first fundus oculi image and a second fundus oculi image by using a third fundus oculi image, the first fundus oculi image being an aberration-corrected image of an eye being examined, the second fundus oculi image being an image having a larger view angle and a lower resolution than the first fundus oculi image, the third fundus oculi image being an image having a smaller view angle and a higher resolution than the second fundus oculi image;
a distance acquiring step of, using a distance acquisition unit, acquiring a distance from a macula lutea of the eye being examined to a certain position in the first fundus oculi image aligned using the alignment unit; and
an evaluating step of, using an evaluation unit, evaluating the state of the eye being examined from the distance and information concerning photoreceptor cells included in the first fundus oculi image.

18. A non-transitory recording medium storing a program for causing a computer to execute the image processing method according to claim 17.

* * * * *